United States Patent
Liu et al.

(10) Patent No.: US 10,973,579 B2
(45) Date of Patent: Apr. 13, 2021

(54) OPTICAL SYSTEM

(71) Applicant: Industrial Technology Research Institute, Hsinchu (TW)

(72) Inventors: Yi-Cheng Liu, Hsinchu County (TW); Yuan-Chin Lee, Hsinchu (TW); De-Yi Chiou, New Taipei (TW); Hung-Chih Chiang, Chiayi (TW)

(73) Assignee: Industrial Technology Research Institute, Hsinchu (TW)

( * ) Notice: Subject to any disclaimer, the term of this patent is extended or adjusted under 35 U.S.C. 154(b) by 48 days.

(21) Appl. No.: 16/234,592

(22) Filed: Dec. 28, 2018

(65) Prior Publication Data

US 2020/0205897 A1 Jul. 2, 2020

(51) Int. Cl.
  *A61B 18/24* (2006.01)
  *A61B 5/00* (2006.01)
  *G02B 27/10* (2006.01)

(52) U.S. Cl.
  CPC ............ *A61B 18/24* (2013.01); *A61B 5/0084* (2013.01); *G02B 27/106* (2013.01)

(58) Field of Classification Search
  CPC ................. A61B 18/24; A61B 5/0084; A61B 2034/2061; A61B 5/6852; A61B 5/0042; A61B 18/00; A61B 2018/00785; A61B 2018/00446; G02B 27/106;
  (Continued)

(56) References Cited

U.S. PATENT DOCUMENTS

| 5,868,734 A * | 2/1999 | Soufiane ........... C03B 37/01248 |
| | | 128/898 |
| 6,567,690 B2 | 5/2003 | Giller et al. |
| 6,618,152 B2 | 9/2003 | Toida |

(Continued)

FOREIGN PATENT DOCUMENTS

| CN | 1853085 | 10/2006 |
| CN | 103068348 | 4/2013 |

(Continued)

OTHER PUBLICATIONS

Hyowon Moon et al., "Fiber-Bragg-grating-based ultrathin shape sensors displaying single-channel sweeping for minimally invasive surgery," Optics and Lasers in Engineering, vol. 59, Apr. 4, 2014, pp. 50-55.

(Continued)

*Primary Examiner* — Gary Jackson
*Assistant Examiner* — Sebastian X Lukjan
(74) *Attorney, Agent, or Firm* — JCIPRNET

(57) ABSTRACT

An optical system adapted to detect an object including a beam splitting and combing element, a catheter, a focusing element, a deformation detecting module, and an object detecting module is provided. The catheter sleeves outside an optical fiber, and the optical fiber has at least one fiber Bragg gratings. The deformation detecting module and the object detecting module are coupled to the beam splitting and combing element. A first light is reflected by the at least one fiber Bragg gratings and then transmitted to the deformation detecting module. A second light is transmitted to and reflected by the object, so as to be transmitted to the object detecting module. A first wavelength range of the first light is different from a second wavelength range of the second light.

10 Claims, 7 Drawing Sheets

(58) Field of Classification Search
CPC ............ G02B 27/1013; G02B 23/2449; G02B 23/2453; G02B 6/02076
See application file for complete search history.

(56) References Cited

U.S. PATENT DOCUMENTS

| | | | |
|---|---|---|---|
| 7,120,481 B2 | 10/2006 | Keller et al. | |
| 7,952,719 B2 | 5/2011 | Brennan, III | |
| 2004/0165810 A1* | 8/2004 | Fujita | A61B 5/061 385/12 |
| 2009/0048588 A1* | 2/2009 | Peng | G02B 6/4415 606/16 |
| 2010/0185187 A1 | 7/2010 | Yamashita et al. | |
| 2014/0340634 A1* | 11/2014 | Kuranov | A61B 3/102 351/206 |
| 2015/0099984 A1* | 4/2015 | Kankaria | G01B 9/0205 600/478 |

FOREIGN PATENT DOCUMENTS

| | | |
|---|---|---|
| CN | 103842768 | 6/2014 |
| CN | 104302241 | 1/2015 |
| CN | 105025829 | 11/2015 |
| CN | 103339485 | 12/2015 |
| CN | 105555205 | 5/2016 |
| CN | 107072717 | 8/2017 |
| CN | 108024838 | 5/2018 |
| JP | 2007151631 | 6/2007 |
| JP | 2018063193 | 4/2018 |
| TW | 201336247 | 9/2013 |
| WO | 2011141829 | 11/2011 |
| WO | 2012168836 | 12/2012 |

OTHER PUBLICATIONS

V Virdyawan et al., "Laser Doppler sensing for blood vessel detection with a biologically inspired steerable needle," Bioinspir. Biomim., vol. 13, Issue 2, Feb. 16, 2018, pp. 1-15.

Raghu Raghavan et al., "Convection-enhanced delivery of therapeutics for brain disease, and its optimization," Neurosurg. Focus, vol. 20, Issue 3, Apr. 2006, pp. 1-13.

Mohamed T. El-Haddad et al., "Advances in intraoperative optical coherence tomography for surgical guidance," Current Opinion in Biomedical Engineering, vol. 3, Sep. 2017, pp. 37-48.

M. Samir Jafri et al., "Optical coherence tomography in the diagnosis and treatment of neurological disorders," Journal of Biomedical Optics, vol. 10, Issue 5, Sep./Oct. 2005, p. 051603-1-p. 051603-11.

"Office Action of Taiwan Counterpart Application," dated Dec. 12, 2019, p. 1-p. 8.

"Office Action of Taiwan Counterpart Application," dated Aug. 5, 2019, p. 1-p. 7.

\* cited by examiner

US 10,973,579 B2

OPTICAL SYSTEM

BACKGROUND

Technical Field

The present disclosure relates to an optical system, and more particularly to an optical detection system.

Description of Related Art

Minimally invasive surgery is a type of surgery performed by surgeons without causing huge wounds to patients through endoscopes and various imaging techniques. The main function of the human brain is responsible for human language, logical thinking, understanding and other functions, and the human brain is a very important and precise organ. If the brain is wounded and needs to be operated, it will be expected that the damage to the brain as small as possible. Because the wounds caused by the minimally invasive surgery are comparatively small, the minimally invasive surgery is the mainstream of future brain surgery.

In the minimally invasive surgery, extremely tiny probes are needed to penetrate the epidermis of the brain, and important brain tissues and blood vessels have to be shunned away during surgery to reach the pathogen accurately. However, existing instruments are difficult to meet the above requirements.

SUMMARY

The present disclosure provides an optical system that can detect a to-be-tested object, learn and record the traveling path of the catheter, and the optical system is suitable for use in minimally invasive surgery.

An embodiment of the present disclosure provides an optical system including a beam splitting and combining element, a catheter, a focusing element, a deformation detecting module, and an object detecting module. The catheter is sleeved outside at least one of the optical fibers, and the optical fiber has at least one fiber Bragg grating. The beam splitting and combining element is disposed at one end of the optical fiber. The focusing element is disposed at the opposite end of the optical fiber. The deformation detecting module is coupled to the beam splitting and combining element. The object detecting module is coupled to the beam splitting and combining element. When a first light having a first wavelength range enters the at least one fiber Bragg grating of the at least one optical fiber through the beam splitting and combining element, the first light is reflected by the at least one fiber Bragg grating to form a first reflected light and returns to the beam splitting and combining element. The first reflected light is split by the beam splitting and combining element and transmitted to the deformation detecting module. When the second light having a second wavelength range enters the fiber Bragg grating of the at least one optical fiber through the beam splitting and combining element, after the second light passes through the at least one fiber Bragg grating and is focused on a to-be-tested object by the focusing element, the second light is reflected by the to-be-tested object to form a second reflected light. The second reflected light sequentially passes through the focusing element, the at least one optical fiber, and the beam splitting and combining element. The second reflected light is split by the beam splitting and combining element and transmitted to the object detecting module. The first wavelength range is different from the second wavelength range.

The above described features and advantages of the present invention will be more apparent from the following description.

DESCRIPTION OF THE EMBODIMENTS

Figure 1:
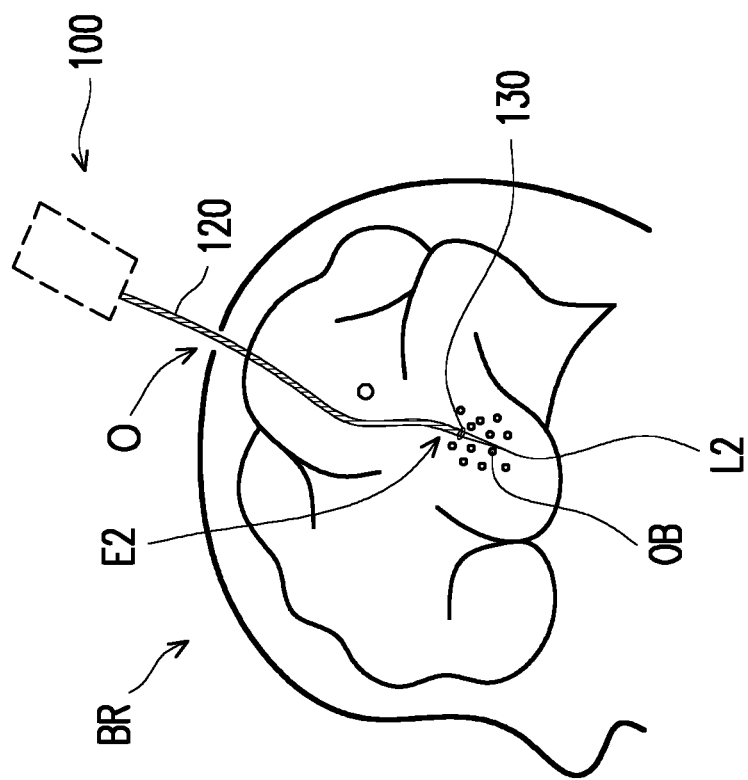
FIG. 1 is a schematic diagram of an optical system for minimally invasive surgery of an embodiment of the present disclosure.
Figure 1:
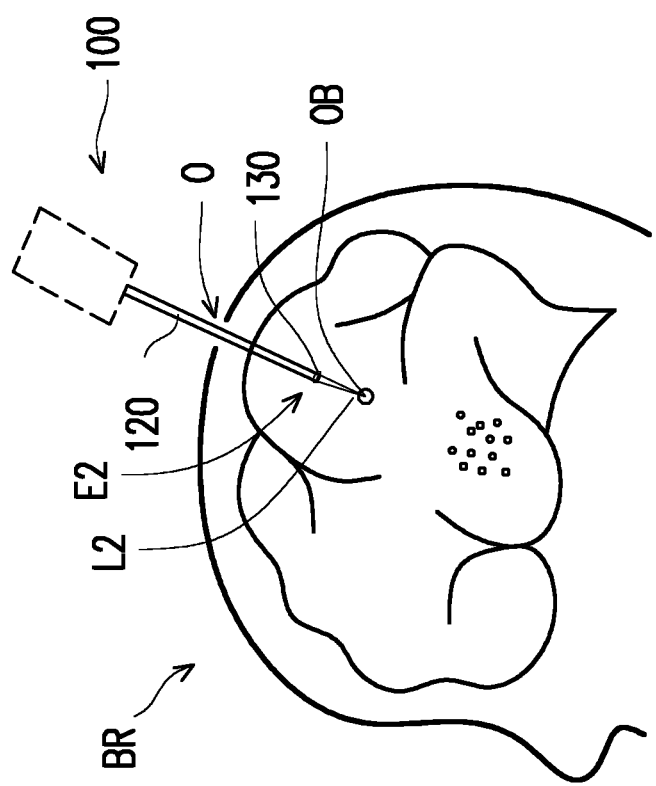
Figure 2:
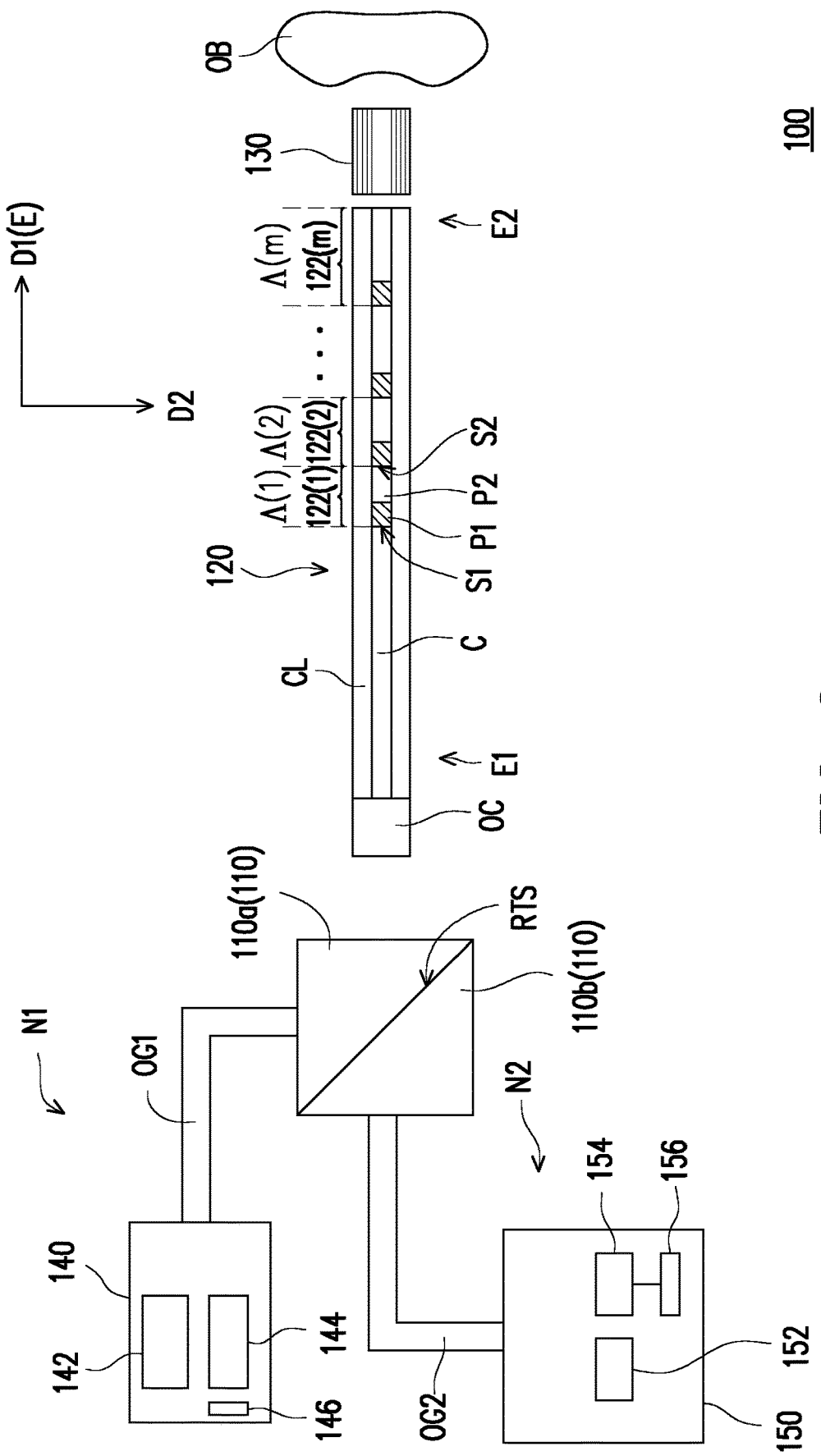
FIG. 2 is a schematic view showing the structure of the optical system of FIG. 1.
Figure 3:
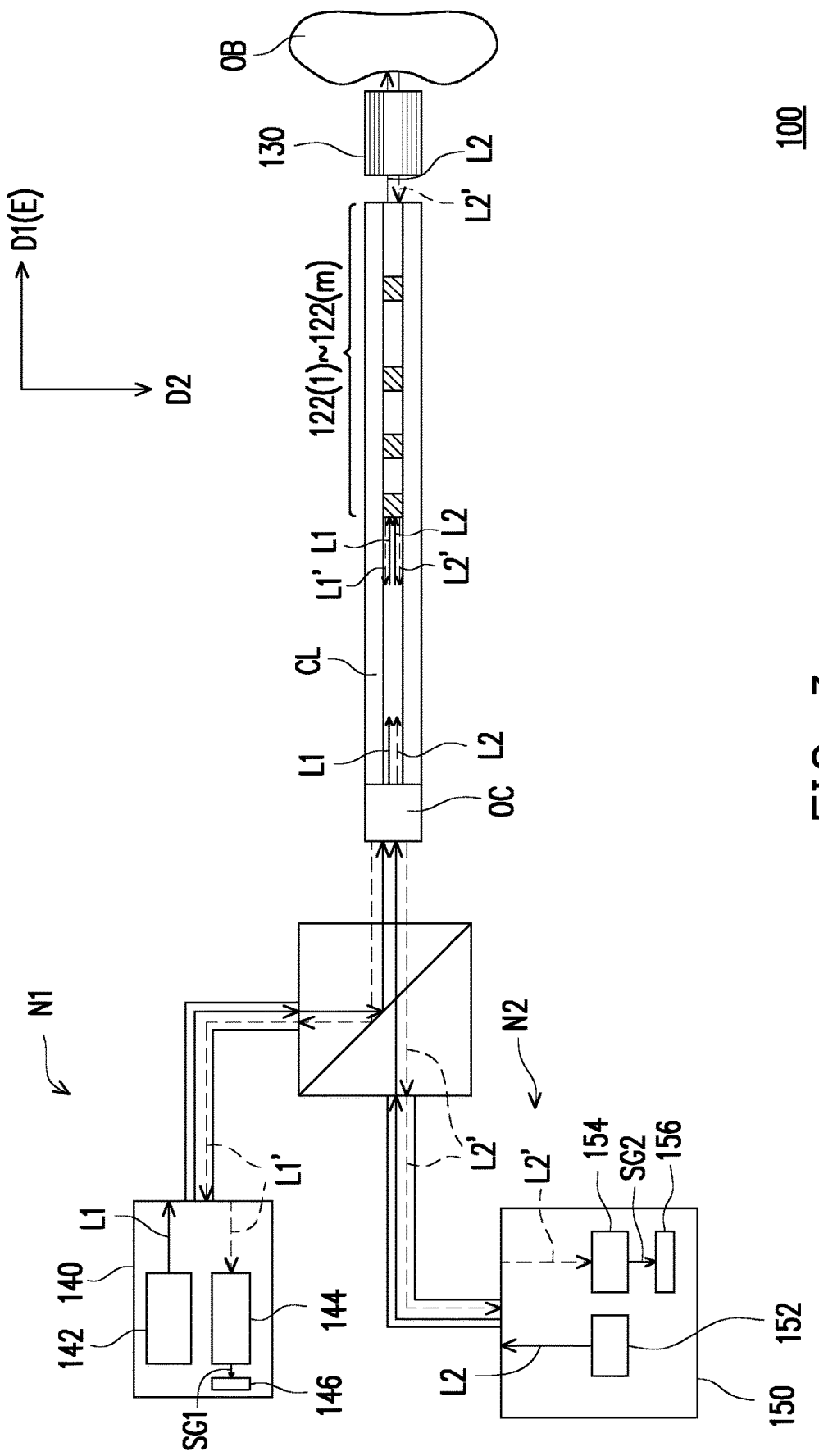
FIG. 3 is a schematic view of the optical path of the first light and the second light in FIG. 2.
Figure 4:
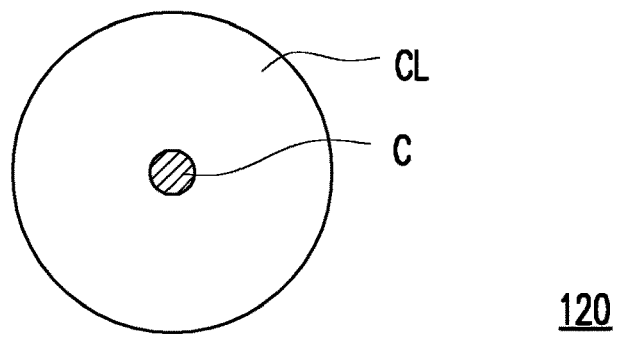
FIG. 4 is a schematic cross-sectional view of an optical fiber in the optical system of FIG. 1.
Figure 5:
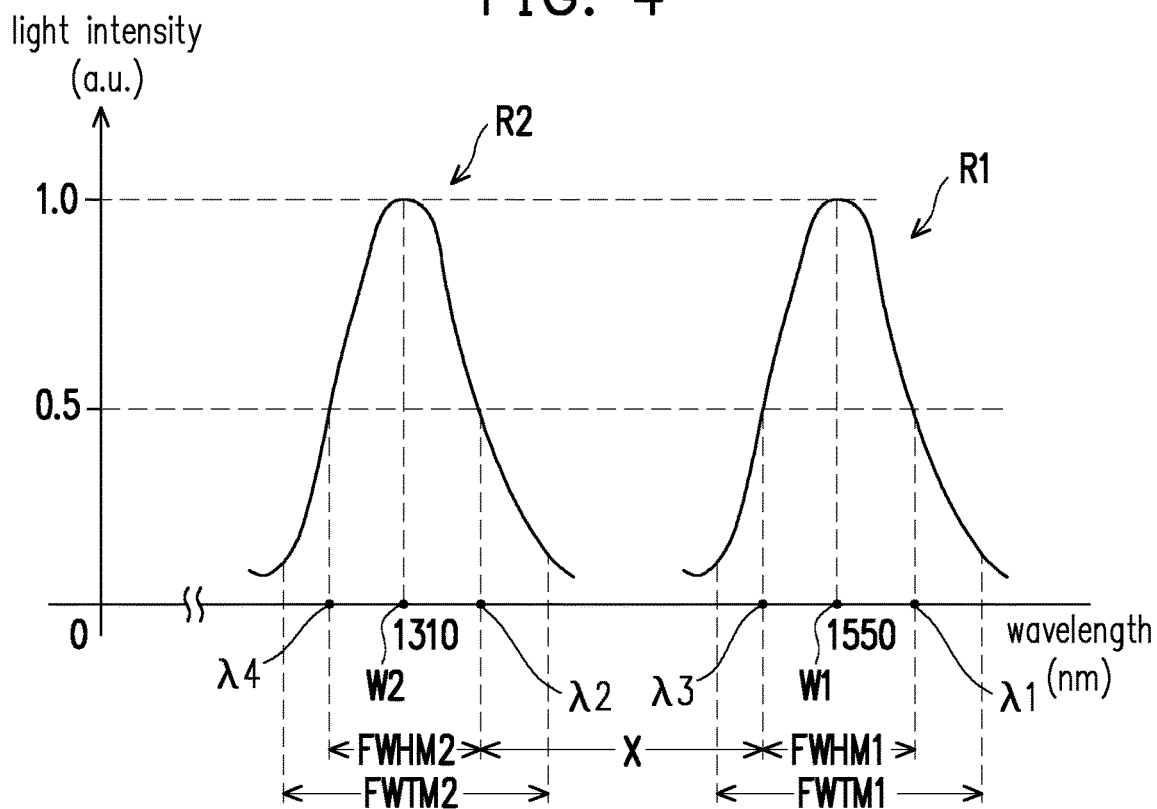
FIG. 5 is a graph of light intensity versus wavelength for a first light and a second light.

FIG. 1 is a schematic diagram of an optical system for minimally invasive surgery of an embodiment of the present disclosure. FIG. 2 is a schematic view showing the structure of the optical system of FIG. 1. FIG. 3 is a schematic view of the optical path of the first light and the second light in FIG. 2. FIG. 4 is a schematic cross-sectional view of an optical fiber in the optical system of FIG. 1. FIG. 5 is a graph of light intensity versus wavelength for a first light and a second light. It should be noted that, for the sake of simplicity, FIG. 1 only shows the optical fiber 120 and the focusing element 130 of FIG. 2 and FIG. 3, and the other elements of FIG. 2 and FIG. 3 are indicated by dashed boxes. FIG. 3 omits partial reference numerals, and other reference numerals may be referred to FIG. 2.

Referring to FIG. 1, FIG. 2, and FIG. 3 in the present embodiment, the optical system 100 is an optical detection system, which is, for example, an optical micro-probe, but is not limited herein. The optical system 100 includes a beam splitting and combining element 110, a catheter (not shown), a focusing element 130, a deformation detecting module 140, and an object detecting module 150. The catheter is sleeved outside the at least one optical fiber 120 having at least one fiber Bragg grating 122 therein. The beam splitting and combining element 110 is disposed at one end E1 of the optical fiber 120. The focusing element 130 is disposed at the opposite end E2 of the optical fiber 120. The deformation detecting module 140 is coupled to the beam splitting and combining element 110. The object detecting module 150 is coupled to the beam splitting and combining element 110. When the first light L1 having a first wavelength range R1 enters the fiber Bragg grating 122 of the optical fiber 120 through the beam splitting and combining element 110, the first light L1 is reflected by the fiber Bragg grating 122 to form a first reflected light L1' and returns to the beam splitting and combining element 110. The first reflected light L1' is split by the beam splitting and combining element 110 and transmitted to the deformation detecting module 140. When the second light L2 having a second wavelength range R2 enters the fiber Bragg grating 122 of the optical fiber 120 through the beam splitting and combining element 110, after the second light L2 passes through the fiber Bragg grating 122 and is focused on the to-be-tested object OB by the focusing element 130, the second light L2 is reflected by the to-be-tested object OB to form a second reflected light L2'. The second reflected light L2' sequentially passes through the focusing element 130, the optical fiber 120, and the beam splitting and combining element 110. The second reflected light L2' is split by the beam splitting and combining element 110 and transmitted to the object detecting module 150. The first wavelength range R1 is different from the second wavelength range R2. The above elements will be described in detail in the following paragraphs.

Referring to FIG. 2 and FIG. 3, the beam splitting and combining element 110 is an optical element configured to combine multiple lights traveling in different optical paths into one light output (combining light function) and divide one light into multiple light outputs traveling in different optical paths (splitting light function). In the embodiment of the present disclosure, the beam splitting and combining element 110 may be a group of prisms that combines the light from different light incident directions (or splits the light from the same incident direction), a dichroic mirror having wavelength selectivity and using different wavelength ranges for splitting the light, or a transflective lens, the disclosure is not limited herein. In the present embodiment, the beam splitting and combining element 110 is a group of prisms including two prisms 110a and 110b. The interface between the two prisms 110a, 110b is a reflective transmissive surface RTS. In other embodiments, the beam splitting and combining element 110 may also be a wavelength-division multiplexing (WDM), and it is not limited to the enumeration.

Referring to FIG. 2, FIG. 3, and FIG. 4, the optical fiber 120 has two ends E1, E2 opposite to each other. The optical fiber 120 includes at least one core C, a cladding layer CL, and a fiber Bragg grating 122. The cladding layer CL coats at least one core C. A fiber Bragg grating (FBG) 122 is installed (written) in the core C. The refractive index of the core C is greater than the refractive index of the outer cladding layer CL. In this embodiment, the number of the at least one core C is one.

Referring to FIG. 2 and FIG. 3, the fiber Bragg grating 122 is an optical element that reflects light having a particular wavelength range and allows transmittance of light having a different wavelength range than this particular wavelength range. In the present embodiment, the number of fiber Bragg gratings 122 is m, wherein m is greater than or equal to 1. These fiber Bragg gratings 122 are disposed along the axial extension direction E of the optical fiber 120. Each fiber Bragg grating 122 includes a first portion P1 and a second portion P2. The refractive index of the first portion P1 is different from the refractive index of the second portion P2. In the embodiment, the refractive index of the first portion P1 is greater than the refractive index of the second portion P2. In other embodiments, the refractive index of the first portion P1 may also be smaller than the refractive index of the second portion P2, and it is not limited herein. The first portion P1 and the second portion P2 are disposed along the axial direction E of the optical fiber 120. From another point of view, the plurality of first portions P1 and the plurality of second portions P2 are alternately arranged in the axial extension direction E and have a distribution of refractive index changes in the core C of the optical fiber 120.

The period Λ of each of the fiber Bragg gratings 122 is defined as the distance of the corresponding first surface S1 of the first portion P1 and the corresponding second surface S2 of the second portion P2 in the axial extension direction E. Taking the first fiber Bragg grating 122(1) from the left in FIG. 2 as an example, the first surface S1 of the first portion P1 faces the one end E1 of the optical fiber. The second surface S2 of the second portion P2 faces the other end E2 of the optical fiber 120. The period Λ(1) of the first fiber Bragg grating 122(1) is the distance between the first surface S1 and the second surface S2 in the axial extension direction E, and the periods of the other fiber Bragg gratings are analogous thereto and not repeated herein. These periods Λ1 to Λm of these fiber Bragg gratings 122(1) to 122(m) are different from each other. In this embodiment, the resonance wavelength is changed by a design of different periods Λ1~Λm, it can be learned that the obtained reflection wavelength range belongs to which fiber Bragg gratings 122(1)~122(m) with the corresponding periods Λ1~Λm. Accordingly, the region where the deformation occurred can be learned.

In another embodiment, each period Λ1~Λm can be designed to be the same, but the first portion P1 contained in each of the fiber Bragg gratings 122(1) to 122(m) has a different refractive index, and the second portion P2 contained in each fiber Bragg grating 122(1)~122(m) has a different refractive index, thereby changing the resonance wavelength. In other embodiments, each period Λ1~Λm may be designed to be the same, but each of the fiber Bragg gratings 122(1)~122(m) has a plurality of portions, and the number of the portions may be two or more. The refractive index of each portion is different, so as to change the resonant wavelength. In another embodiment, the periods, the refractive index of each fiber Bragg grating corresponding to the same portion, and the refractive index of each fiber Bragg grating having a plurality of portions are designed to be changed, thereby changing the resonant wavelength. It is not limited to the enumeration.

Referring to FIG. 1, FIG. 2, and FIG. 3, the focusing element 130 is an optical element that focuses light. In the embodiment of the present disclosure, the focusing element 130 can be a gradient-index (GRIN) lens, a single convex lens, a single Fresnel converging lens, or an optical focusing lens composed of a plurality of convex and concave lenses having different diopters. In the present embodiment, the focusing element 130 is a GRIN lens.

Referring to FIG. 2 and FIG. 3, the deformation detecting module 140 is configured to detect deformation. The deformation detecting module 140 is an optical detecting module, and is, for example, an optical transceiver module. In detail, the deformation detecting module 140 includes a first light source 142, a first optical sensor 144, and a first processor 146. The first light source 142 is adapted to emit a first light L1. The first optical sensor 144 is adapted to receive the light L1' transmitted from the optical fiber 120 to the deformation detecting module 140 and convert the light L1' into the first electrical signal SG1. The first processor 146 receives the first electrical signal SG1 from the first optical sensor 144 and performs analysis accordingly.

Referring to FIG. 2 and FIG. 3, the object detecting module 150 is configured to detect a to-be-tested object OB located at one end E2 of the optical fiber 120. The object detecting module 150 is an optical detecting module, and is, for example, an optical transceiver module. The structure of the object detecting module is similar to the deformation detecting module 140. In detail, the object detecting module 150 includes a second light source 152, a second optical sensor 154, and a second processor 156. The second light source 152 is adapted to emit a second light L2. The second optical sensor 154 is adapted to receive the light L2' transmitted from the optical fiber 120 to the object detecting module 150 and converts the light L2' into the second electrical signal SG2. The second processor 156 receives the second electrical signal SG2 from the second optical sensor 154 and performs analysis accordingly. In the embodiment of the present disclosure, the object detecting module 150 is, for example, an optical coherence tomography (OCT) detection module, a Doppler image module, or an absorption spectrum module, but it is not limited herein. In this embodiment, the object detecting module 150 is an optical coherence tomography detection module.

Referring to FIG. 2 and FIG. 3, in the embodiment of the present disclosure, the types of the first and second light sources 142 and 152 may be a laser diode (LD), a light emitting diode (LED), an organic light emitting diode (OLED), a superluminescent diode (SLED or SLD), or other types of light-emitting elements, or the array arranged by the above-mentioned same type or different types of light-emitting elements, but it is not limited herein. In this embodiment, the first and second light sources 142, 152 include laser diodes. Referring to FIG. 5, the first light source 142 is different from the second light source 152 in that the first light L1 emitted by the first light source 142 has a first wavelength range R1. The second light L2 emitted by the second light source 152 has a second wavelength range R2. The first wavelength range R1 is different from the second wavelength range R2.

Referring to FIG. 5, in detail, the first peak wavelength W1 of the first wavelength range R1 is different from the second peak wavelength W2 of the second wavelength range R2. The peak wavelength refers to the wavelength corresponding to the strongest light intensity in the light intensity distribution in this wavelength range. In the present embodiment, the first peak wavelength W1 is, for example, 1550 nm, and the second peak wavelength W2 is, for example, 1310 nm, but the disclosure is not limited herein.

The first wavelength range R1 has a first full width at half maximum FWHM1, and the first full width at half maximum FWHM1 is defined by the first wavelength $\lambda 1$ and the third wavelength $\lambda 3$. The second wavelength range R2 has a second full width at half maximum FWHM2, and the second full width at half maximum FWHM2 is defined by the second wavelength $\lambda 2$ and the fourth wavelength $\lambda 4$. The above-mentioned full width at half maximum is defined as the difference between the wavelength values of the two end points corresponding to one-half of the peak in the light intensity distribution of the wavelength range of the light. The mentioned first wave 21 and third wavelength $\lambda 3$ are the wavelength values of the two end points of the first full width at half maximum FWHM1, and the second wavelength $\lambda 2$ and the fourth wavelength $\lambda 4$ are the wavelength values of the two end points of the second full width at half maximum FWHM2. The first wavelength $\lambda 1$ is greater than the third wavelength $\lambda 3$. The second wavelength $\lambda 2$ is greater than the fourth wavelength $\lambda 3$. The first full width at half maximum FWHM1 has a first peak wavelength W1, and the first peak wavelength W1 is smaller than the first wavelength $\lambda 1$ and greater than the third wavelength $\lambda 3$. The second full width at half maximum FWHM2 has a second peak wavelength W2, and the second peak wavelength W2 is smaller than the second wavelength $\lambda 2$ and greater than the fourth wavelength $\lambda 4$. The first peak wavelength W1 is greater than the second peak wavelength W2. In this embodiment, the third wavelength $\lambda 3$ is greater than the second wavelength $\lambda 2$. The absolute value of the difference X between the third wavelength $\lambda 3$ and the second wavelength $\lambda 2$ is greater than 50 nm. In another embodiment, the first wavelength range R1 has a first full width at tenth maximum FWTM1, and the second wavelength range R2 has a second full width at tenth maximum FWTM2. Wherein the wavelength range of the first full width at tenth maximum FWTM1 of the positive/negative one-half of the first peak wavelength W1(W1±FWTM1/2) and the wavelength range of the second full width at tenth maximum FWTM2 of the positive/negative one-half of the second peak wavelength W2 (W2±FWTM2/2) are not overlapped with each other.

Referring to FIG. 2 and FIG. 3, in the embodiment, the first and second optical sensors 144 and 154 are photoelectric elements for converting optical signals into electrical signals, and the types thereof include a photodiode (PD), a photo resistance cell, a complementary metal-oxide-semiconductor (CMOS), a photoelectric inductor, and an avalanche photodiode (APD), the present disclosure is not limited herein.

Referring to FIG. 2 and FIG. 3, in the embodiment, the first and second processors 146 and 156 may be a computer, a micro controller unit (MCU), or a central processing unit (CPU), or other programmable controllers, such as microprocessors, a digital signal processor (DSP), a programmable controller, an application specific integrated circuits (ASIC), a programmable logic device (PLD), or other similar devices, the disclosure is not limited herein. In this embodiment, the first and second processors 146 and 156 are computers.

Referring to FIG. 2 and FIG. 3, in addition, in the embodiment, the optical system 100 can be selectively configured with the light guiding elements OG1, OG2 and the optical coupler OC. The light guiding element OG1 is disposed between the deformation detecting module 140 and the beam splitting and combining element 110. The light guiding element OG2 is disposed between the object detecting module 150 and the beam splitting and combining element 110. The optical coupler OC is disposed between the beam splitting and combining element 110 and the end E1 of the optical fiber 120. In this embodiment, the light guiding element OG1 is used to optically couple the deformation detecting module 140 with the beam splitting and combining element 110, and the light guiding element OG2 is used to optically couple the object detecting module 150 with the beam splitting and combining element 110. The optical coupler OC is used to optically couple the beam splitting and combining element 110 with the optical fiber 120. Here, the term "optical coupling" between two elements means that the light beam transmitted in the element A can enter the element B and vice versa. In this embodiment, the light guiding elements OG1, OG2 may be optical fibers. In an embodiment, the light guiding elements OG1, OG2 may also be mirrors.

In the following paragraphs, the arrangement between the elements from the upstream of the optical path to the downstream of the optical path in the optical system 100 will be described in detail.

Referring to FIG. 2 and FIG. 3, the deformation detecting module 140 and the object detecting module 150 are disposed on different sides N1 and N2 of the beam splitting and combining element 110 and respectively optically coupled with the beam splitting and combining element 110 through the light guiding elements OG1 and OG2. The beam splitting and combining element 110 is disposed at one end E1 of the optical fiber 110. The focusing element 130 is disposed at the other end E2 of the optical fiber 120, and the focusing element 130 is located between the to-be-tested object OB and the optical fiber 120.

In the following paragraphs, the principle of operation of the optical system 100 will be described in detail by referring to FIG. 1 through FIG. 3.

Referring to the partial drawing on the left in FIG. 1, FIG. 2, and FIG. 3, the optical fiber 120 of the optical system 100 and the focusing element 130 pass through the inlet O to enter the brain BR of the patient. As the fiber 120 advances into the interior of the brain BR, the fiber 120 will correspondingly deform differently at different times, and a variety of different to-be-tested objects OB will be encountered in front of one end E2 of the fiber 120. The deformation detecting module 140 is configured to detect deformation of the optical fiber 120 during traveling. The object detecting module 150 is configured to detect the to-be-tested object OB. The deformation detecting function and the object detecting function are explained in the following paragraphs.

First, it is a description of the deformation detecting function.

Referring to the partial drawing on the left in FIG. 1, FIG. 2, and FIG. 3, after the optical fiber 120 enters the brain BR, the first light source 142 in the deformation detecting module 140 is turned on to emit the first light L1. The first light L1 is guided by the light guiding element OG1 and enters the beam splitting and combining element 110 in the light incident direction of the direction D2. Then, the first light L1 is reflected by the reflective transmissive surface RTS and sequentially enters the optical coupler OC and the optical fiber 120. The first light L1 performs one to more total internal reflection (TIR) in the core C of the optical fiber 120, then the first light L1 is transmitted to these fiber Bragg gratings 122.

Since these fiber Bragg gratings 122 have different periods A, these fiber Bragg gratings 122 are designed to reflect a specific plurality of wavelengths ($\lambda_c$) in the first wavelength range R1 in an initial state (i.e., a state in which the fibers 120 are not deformed). For example, in the initial state, the first fiber grating 122(1) is, for example, for reflecting light of a specific wavelength $\lambda_{c1}$ of 1550 nm, and the second fiber grating 122(2) is, for example, for reflecting light of a specific wavelength $\lambda_{c2}$ of 1555 nm, and so forth, the present disclosure is not limited herein. The specific wavelength that each fiber Bragg grating 122 can reflect is determined by its corresponding period $\Lambda$. It should be noted that the above-mentioned numbers are only examples, and the disclosure is not limited herein. The set of values of the specific wavelengths $\lambda_{c1}$~$\lambda_{cm}$ that can be reflected by these fiber Bragg gratings 122 in the initial state is the initial set S0, as follows:

($\lambda_{c1},\lambda_{c2},\lambda_{c3}, \ldots ,\lambda_{cm}$)→initial set S0.

Then, in the deformed state (i.e., when the optical fiber 120 is subjected to an external force to cause deformation itself), the period $\Lambda$ of the fiber Bragg gratings 122 respectively has a corresponding change, more or less. That is, the period changes from $\Lambda$ to $\Lambda+\Delta\Lambda$, where $\Delta\Lambda$ can be positive value, negative value, or zero. Therefore, the specific wavelength $\lambda_c$ that can be reflected by each of the fiber Bragg gratings 122 also changes correspondingly. That is, the specific wavelength that can be reflected changes from $\lambda_c$ to $\lambda_c'$, where $\lambda_c'=\lambda_c+\Delta\lambda_c$. The set of values of the specific wavelengths $\lambda_{c1}'$~$\lambda_{cm}'$ that can be reflected by these fiber Bragg gratings 122 in the deformed state is the deformation set DS, as follows:

($\lambda_{c1}',\lambda_{c2}',\lambda_{c3}' \ldots ,\lambda_{cm}'$)→deformation set DS.

Referring to FIG. 3, thus, a portion of the first light L1 is reflected by the fiber Bragg gratings 122 to form a first reflected light L1'. The first reflected light L1' sequentially passes through the optical fiber 120, the optical coupler OC. Then, the first reflected light L1' is split by the beam splitting and combining element 110 and transmitted to the first optical sensor 144 of the deformation detecting module 140. The first optical sensor 144 converts the first reflected light L1' into the first electrical signal SG1. Next, the first processor 146 performs analysis according to the first electrical signal SG1.

Specifically, when the optical fiber 120 is subjected to an external force and is in a deformed state, the period $\Lambda$ of each of the fiber Bragg gratings 122 varies, and the specific wavelength that can be reflected is also changed from $\lambda_{c1}$~$\lambda_{cm}$ (i.e., the initial set S0) to $\lambda_{c1}'$~$\lambda_{cm}'$ (i.e., the deformation set DS). The first optical signal SG1 is provided with information of the deformation set DS. The first processor 146 obtains a wavelength variation set WVS according to the values of difference between the initial set S0 and the deformation set DS, as follows:

($\Delta\lambda_{c1},\Delta\lambda_{c2},\Delta\lambda_{c3}, \ldots ,\Delta\lambda_{cm}$)→wavelength variation set WVS.

Since these fiber Bragg gratings 122 are distributed in the core C, the overall deformation of the optical fiber 120 can be estimated by calculating the deformation of the fiber Bragg gratings 122 corresponding to the respective regions. The first processor 146 then calculate the deformation of the regions in which the respective fiber Bragg gratings 122 respectively correspond to at a specific time according to the wavelength variation set WVS.

As the above-mentioned, since the deformation of the optical fiber 120 is a time varying function, that is, the above-described deformation set DS(t) and the wavelength variation set WVS(t) are also time-varying (related to time t). Thus, the deformation detecting module 140 can calculate the corresponding wavelength variation set WVS(t) at different times. Accordingly, the deformation of the optical fiber 120 at different times is obtained, whereby the position of the optical fiber 120 in the brain BR can be estimated. More specifically, by the deformation of the optical fiber 120 at different times, it is possible to roughly infer parameters of the distance that the optical fiber 120 travels into the brain BR and the turning directions of the optical fiber 120. Accordingly, the traveling path of the catheter (optical fiber 120) in the brain BR can be learned to estimate the position of the optical fiber 120 in the brain BR. Moreover, the deformation detecting module 140 further has a storage device for storing/recording the traveling path of the catheter (optical fiber 120).

Next, it is a description of the object detecting function.

Referring again to the left part of FIG. 1, FIG. 2, and FIG. 3, when the optical fiber 120 enters the brain BR, the second light source 152 in the object detecting module 150 is turned on to emit the second light L2. The second light L2 is guided by the light guiding element OG2 and enters the beam splitting and combining element 110 in the light incident direction of the direction D1. Then, the second light L2 passes through the reflective transmissive surface RTS into the optical coupler OC and the optical fiber 120 sequentially. The second light L2 performs one to more total internal reflections in the core C of the optical fiber 120 and passes through the fiber Bragg gratings 122 to emit the light at one end E2 of the optical fiber 120. The second light L2 is focused by the focusing element 130 to be transmitted to the to-be-tested object OB and reflected by the to-be-tested object OB to form a second reflected light L2'. The second reflected light L2' sequentially passes through the focusing element 130, the optical fiber 120, the optical coupler OC. The second reflected light L2' is split by the beam splitting and combining element 110 and transmitted to the second light sensor 154 in the object detecting module 150. The second optical sensor 154 converts the second reflected light L2' into the second electrical signal SG2. Next, the second processor 156 performs analysis according to the second electrical signal SG2.

In this embodiment, the object detecting module 150 is an optical coherence tomography detection module. In an embodiment, the optical coherence tomography detection module can learn the tomographic images at different depths in a direction parallel to the transmission direction D1 of the light L2 according to the second electrical signal SG2 and the longitudinal scan (A scan), so as to learn the specific pattern of the to-be-tested object OB. In another embodiment, the optical coherence tomography detection module can learn the tomographic image in a direction D2 perpendicular to the transmission direction D1 of the light L2 according to the second electrical signal SG2 and the transversal scan (B scan). In still another embodiment, the optical coherence tomography detection module can combine the longitudinal scanning and the transversal scanning according to the second electrical signal SG2 to learn the tomographic image. The longitudinal direction mentioned above is, for example, the transmission direction D1 of the light L2 in the optical fiber 120, and the transversal direction is, for example, a direction D2 perpendicular to the transmission direction D1 of the light L2 in the optical fiber 120. If it is determined by the tomographic image that the to-be-tested object OB is a blood vessel, the to-be-tested object OB is determined to be an obstacle, and the object detecting module 150 can inform the user to control the catheter to bypass the blood vessel to avoid intracerebral hemorrhage. Next, referring to the right diagram in FIG. 1, the paths of the catheter (optical fiber 120) can be corrected one or more times as described above, and finally the lesion or target in the brain BR is found by the tomographic image.

In another embodiment, the object detecting module 150 can be a Doppler image module. The Doppler image module can determine whether or not the to-be-tested object OB having flowing blood by Doppler effect, the second light L2, and the second reflected light L2', so as to determine whether the to-be-tested object OB is blood vessel or not.

In another embodiment, the object detecting module 150 can be an absorption spectrum module. When the second light L2 is transmitted to the to-be-tested object OB, part of the second light L2 is absorbed by the to-be-tested object OB, and part of the second light L2 is reflected back to form the second reflected light L2'. Since the absorbance of light is varied in different tissues of the brain BR (for example, blood vessels, blood vessel walls, or a cerebral cortex), the absorption spectrum module can compare the spectrums of the original second light L2 and the reflected second reflected light L2', thereby the composition of the to-be-tested object OB can be determined by the spectrum of the second reflected light L2'.

In this embodiment, the first light L1 and the second light L2 are transmitted in the same core C in the optical fiber 120. That is, the first light L1 and the second light L2 share a core C.

In the present embodiment, the number of fiber Bragg gratings 122 is plural. In other embodiments, the number of the fiber Bragg gratings 122 may also be one, and the disclosure is not limited herein. Further, in FIG. 2 and FIG. 3, the position of the installation region in which the fiber Bragg grating 122 is distributed in the core C is, for example, close to the one end E2 of the optical fiber 120. In other embodiments, the position of the installation region of the fiber Bragg grating 122 distributed in the core C may also be other area in the core C, and the disclosure is not limited herein.

As described above, in the optical system 100 of the present embodiment, the deformation detecting module 140 can learn the traveling path of the catheter (optical fiber 120) by detecting the deformation of the optical fiber 120 through the first light L1, and can further record the traveling path of the catheter (optical fiber 120). The object detecting module 150 detects the to-be-tested object OB by the second light L2. In an embodiment, the deformation detecting module 140 and the object detecting module 150 can respectively emit the first light L1 and the second light L2 at the same time for detection, so that the optical system 100 can simultaneously have the functions of detecting the to-be-tested object OB and learning the traveling path of the catheter (of the optical fiber 120). In addition, since the first wavelength range R1 of the first light L1 is different from the second wavelength range R2 of the second light L2, the deformation detection result of the deformation detecting module 140 and the object detection result of the object detecting module 150 are comparatively less mutual interference, thereby the detection results are more accurate.

Moreover, when the optical system 100 of the present embodiment is used for minimally invasive surgery of the brain and the object detecting module 150 detects that the to-be-tested OB of the optical fiber 120 is a lesion, the traveling path of the catheter (optical fiber 120) can be used to determine the specific location of the lesion within the brain BR.

In addition, in an embodiment, since the same optical fiber 120 is shared in the deformation detection and the object detection, the number of the optical fibers 120 disposed in the catheter can be reduced, and the catheter having a smaller diameter can be used, so the catheter is suitable for minimally invasive surgery.

It is to be noted that the following embodiments use the same reference numerals and parts of the above-mentioned embodiments, and the same reference numerals are used to refer to the same or similar elements, and the description of the same technical content is omitted. For the description of the omitted portions, reference may be made to the foregoing embodiments, and the following embodiments are not repeated.

Figure 6:
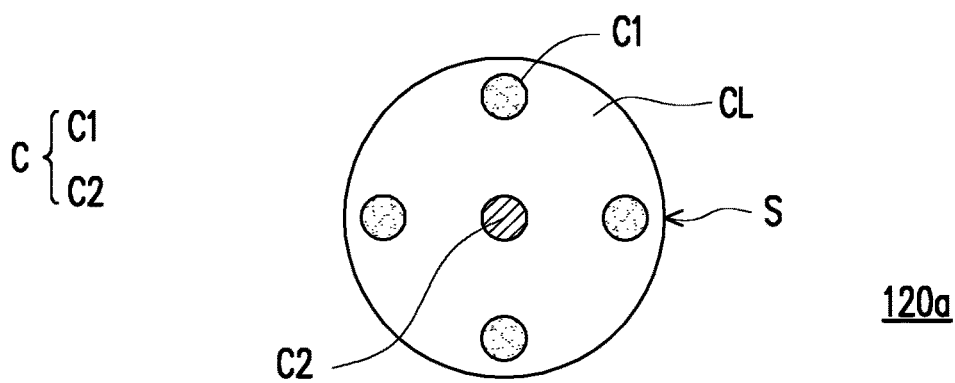
FIG. 6 is a schematic cross-sectional view showing another embodiment of the optical fiber.

FIG. 6 is a schematic cross-sectional view showing another embodiment of the optical fiber.

Referring to FIG. 6, the optical fiber 120a of FIG. 6 is similar to the optical fiber 120 of FIG. 1. It should be noted, however, that the number of cores C of the optical fiber 120a in FIG. 6 is plural. These cores C include at least one first core C1 and at least one second core C2. For example, the number of the first core C1 is four, and the number of the at least one second core C2 is one, but it is not limited herein. In this embodiment, the first light L1 is transmitted through the first core C1 in the optical fiber 120a. The second light L2 is transmitted through the second core C2 in the optical fiber 120a. In short, in the present embodiment, the first cores C1 and the second core C2 respectively used by the first light L1 and the second light L2 in the optical fiber 120a for transmittance are different. That is, the first light L1 and the second light L2 do not share the same core.

In this embodiment, the plurality of first cores C1 are used, so that the deformation detecting module 140 may reply on the average of the returned results of the plurality of the first electrical signal SG1 correspondingly obtained from the plurality of first reflected light L1' in the first cores C1 to make the deformation detection result more accurate.

In other embodiments, only the first cores C1 disposed near the surface S may be used. The first light L1 and the second light L2 are transmitted through these first cores C1 in the optical fiber 120a, that is, the first light. L1 and second light L2 share the same core C1 without using the second core C2. Alternatively, in other embodiments, the second core C2 may also be used to transmit the first light L1 and the second light L2, and the remaining first core C1 is not used or only partially used, and it is not limited to the enumeration.

Figure 7:
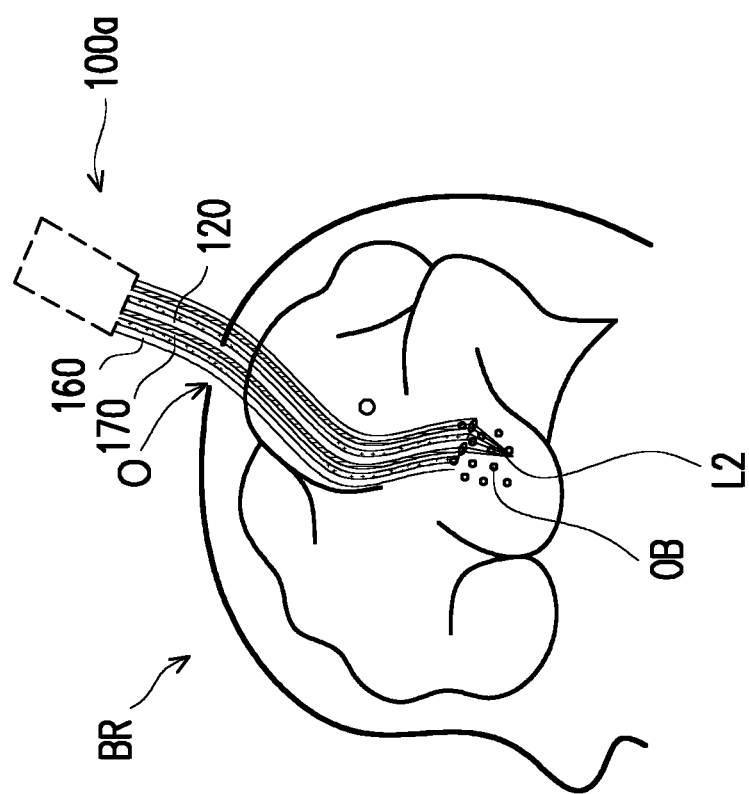
FIG. 7 is a schematic diagram of an optical system for minimally invasive surgery of the brain according to another embodiment of the present disclosure.
Figure 7:
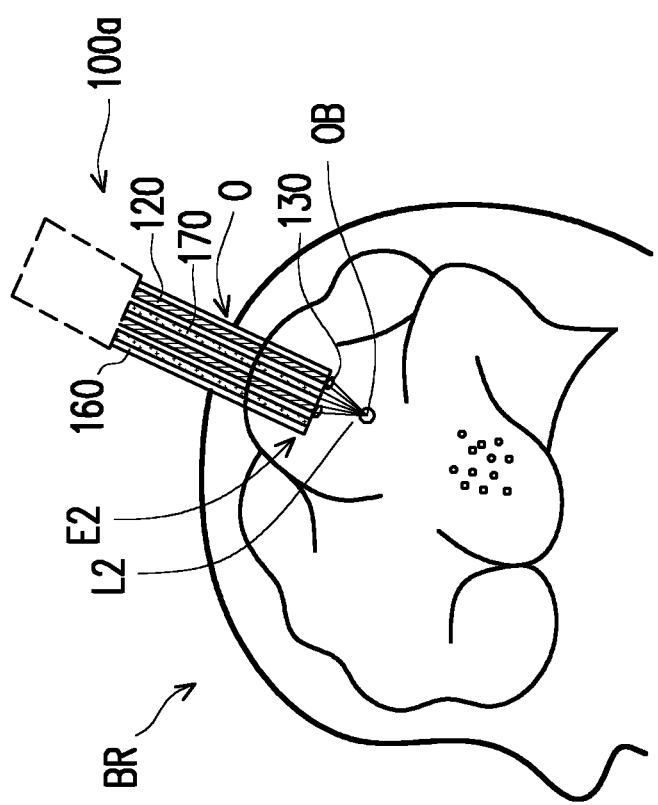
Figure 8:
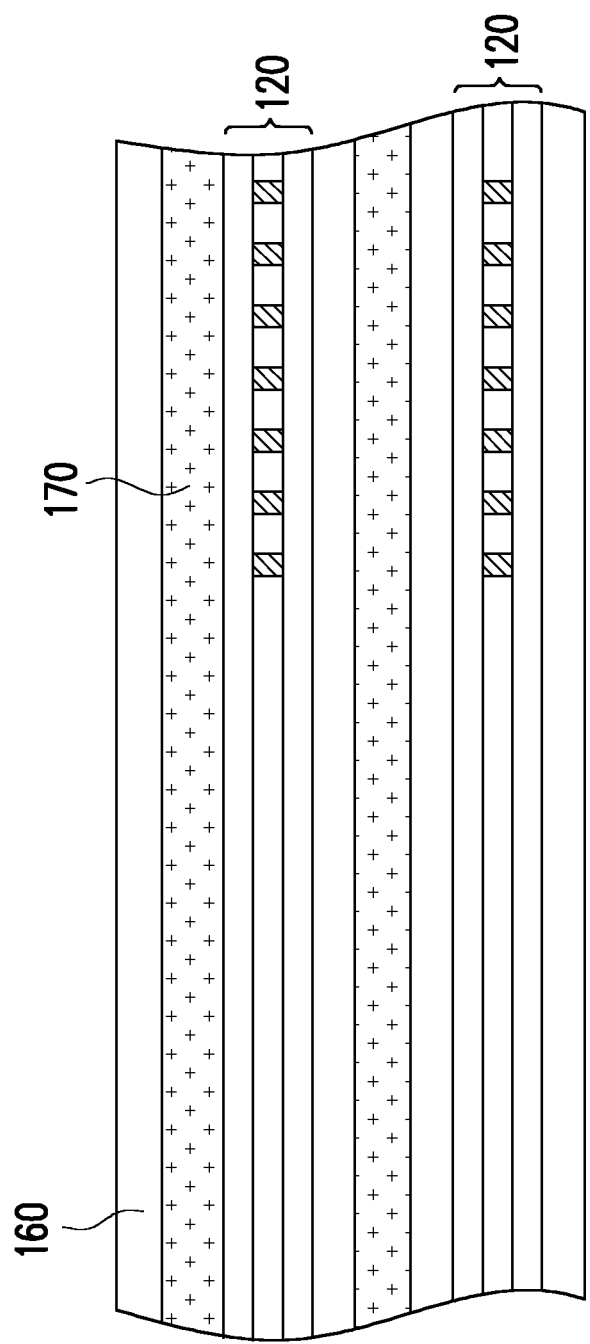
FIG. 8 is a partial longitudinal cross-sectional view of the optical fiber, the functional tube, and the catheter of FIG. 7.
Figure 9:
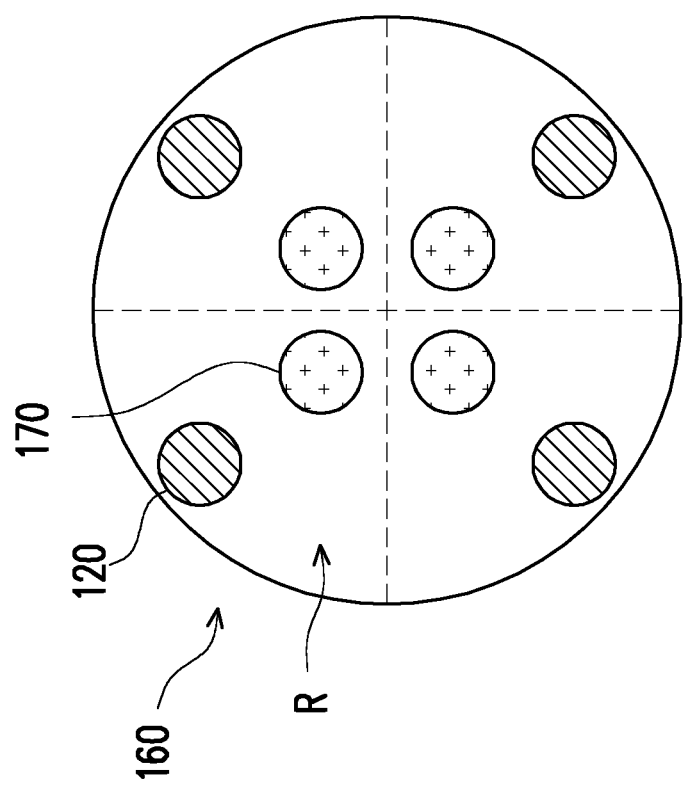
FIG. 9 is a cross-sectional view of the optical fiber, the functional tube and the catheter of FIG. 7 and FIG. 8.

FIG. 7 is a schematic diagram of an optical system for minimally invasive surgery of the brain according to another embodiment of the present disclosure. FIG. 8 is a partial longitudinal cross-sectional view of the optical fiber, the functional tube, and the catheter of FIG. 7. FIG. 9 is a cross-sectional view of the optical fiber, the functional tube, and the catheter of FIG. 7 and FIG. 8.

Referring to FIG. 7 through FIG. 9, the optical system 100a is substantially similar to the optical system 100 of FIG. 1 through FIG. 3. It should be noted, however, that in FIG. 7 through FIG. 9, the optical system 100a further includes a catheter 160 and a plurality of functional tubes 170. The number of at least one optical fiber 120 is plural. The catheter 160 has a plurality of regions R therein. A functional tube 170 and an optical fiber 120 are disposed in each of the regions R. By the above-mentioned deformation acquisition method, the deformation detecting module 140 can correspondingly calculate the deformation of each region R to learn the precise deformation of the catheter 160. In the present embodiment, the diameter of the catheter 160 is, for example, less than 6 millimeters (mm), but it is not limited herein. The functional tube 170 refers to a catheter that is used to perform different functions. In an embodiment, the functional tubes 170 having different functions may be provided in different regions R, and different functions of the functional tubes 170 will be exemplified in the following paragraphs.

Next, referring to the right diagram of FIG. 7, when the catheter (optical fiber 120) can be moved to the vicinity of the lesion in the brain BR after one or more path corrections, the drug can be put into the vicinity of the lesion by the functional tube 170. At this time, the functional tube 170 serves as a drug delivery tube.

In another embodiment, if there is a blood clot in the brain BR, the blood clot can be extracted by connecting the functional tube 170 to an air extracting device (not shown).

In another embodiment, the electrode is placed by the functional tube 170 to penetrate deep into the deep brain tissue, subthalamic nucleus (STN), for treatment of Parkinson's disease.

Further, it should be noted that, for convenience of explanation, in the above-described embodiment, the optical system 100 is used as a probe and is used for minimally invasive surgery of the brain, but this is for illustrative purposes. The optical system 100 of the embodiment of the present disclosure may also be used as other types of elements or for other purposes, and the disclosure is not limited herein.

In summary, in the optical system of the embodiment of the present disclosure, at least one fiber Bragg grating is disposed in the optical fiber, and the at least one fiber Bragg grating is used to reflect the first light having the first wavelength range. When the optical fiber is deformed by an external force, the deformation detecting module can know the deformation of the optical fiber by the reflected first reflected light, thereby further learning the traveling path of the catheter. On the other hand, the second light emitted by the object detecting module can also be transmitted to the to-be-tested object by the optical fiber, and the object detecting module receives the second reflected light reflected by the to-be-tested object to determine the specific pattern of the to-be-tested object. In addition, the first wavelength range of the first light is different from the second wavelength range of the second light, so the deformation detection result of the deformation detecting module and the object detection result of the object detecting module are comparatively less interfered with each other.

The present disclosure has been disclosed in the above embodiments, but it is not intended to limit the disclosure, and any one of ordinary skill in the art can make some changes and refinements without departing from the spirit and scope of the disclosure. The scope of protection of this disclosure is subject to the definition of the scope of the appended claims.

What is claimed is:

1. An optical system adapted to detect a to-be-tested object, comprising:
   a beam splitting and combining element;
   a catheter sleeved outside at least one optical fiber, the optical fiber having at least one fiber Bragg grating, and the beam splitting and combining element disposed at one end of the optical fiber;
   a focusing element disposed at the opposite end of the optical fiber;
   a deformation detecting module coupled to the beam splitting and combining element; and
   an object detecting module coupled to the beam splitting and combining element,
   wherein when a first light having a first wavelength range enters the at least one fiber Bragg grating of the at least one optical fiber through the beam splitting and combining element, the first light is reflected by the at least one fiber Bragg grating to form a first reflected light and returns to the beam splitting and combining element, the first reflected light is split by the beam splitting and combining element and transmitted to the deformation detecting module,
   when a second light having a second wavelength range enters the at least one fiber Bragg grating of the at least one optical fiber through the beam splitting and combining element, after the second light passes through the at least one fiber Bragg grating and is focused on the to-be-tested object by the focusing element, the second light is reflected by the to-be-tested object to form a second reflected light, the second reflected light sequentially passes through the focusing element, the at least one optical fiber, and the beam splitting and combining element, the second reflected light is split by the beam splitting and combining element and transmitted to the object detecting module,
   wherein the first wavelength range is different from the second wavelength range, has a first full width at half maximum defined by a first wavelength and a third wavelength in the first wavelength range, and the first wavelength is greater than the third wavelength;
   the second wavelength range has a second full width at half maximum defined by a second wavelength and a fourth wavelength in the second wavelength range, the second wavelength is greater than the fourth wavelength;

the first full width at half maximum has a first peak wavelength, and the first peak wavelength is smaller than the first wavelength and greater than the third wavelength;

the second full width at half maximum has a second peak wavelength, and the second peak wavelength is smaller than the second wavelength and greater than the fourth wavelength; and the first peak wavelength is greater than the second peak wavelength, and an absolute value of a difference between the third wavelength of the first full width at half maximum and the second wavelength of the second full width at half maximum is greater than 50 nm.

2. The optical system of claim 1, wherein the at least one optical fiber comprises at least one core and a cladding layer, the cladding layer coats the at least one core, and the at least one fiber Bragg grating is disposed in the at least one core.

3. The optical system of claim 2, wherein a refractive index of the at least one core is greater than a refractive index of the cladding layer.

4. The optical system of claim 2, wherein the number of the at least one core is one, wherein the first light and the second light are transmitted in the optical fiber by the core.

5. The optical system of claim 2, wherein the number of the at least one core is plural, the cores comprise at least one first core and at least one second core, wherein the first light is transmitted in the optical fiber through the at least one first core, and the second light is transmitted in the optical fiber through the at least one second core.

6. The optical system of claim 5, wherein the at least one first core is disposed adjacent a surface of the optical fiber.

7. The optical system of claim 1, wherein the object detecting module is an optical coherence tomography module, a Doppler image module, or an absorption spectrum module.

8. An optical system adapted to detect a to-be-tested object, comprising:
 a beam splitting and combining element;
 a catheter sleeved outside at least one optical fiber, the optical fiber having at least one fiber Bragg grating, and the beam splitting and combining element disposed at one end of the optical fiber;
 a focusing element disposed at the opposite end of the optical fiber;
 a deformation detecting module coupled to the beam splitting and combining element; and
 an object detecting module coupled to the beam splitting and combining element,
 wherein when a first light having a first wavelength range enters the at least one fiber Bragg grating of the at least one optical fiber through the beam splitting and combining element, the first light is reflected by the at least one fiber Bragg grating to form a first reflected light and returns to the beam splitting and combining element, the first reflected light is split by the beam splitting and combining element and transmitted to the deformation detecting module,
 when a second light having a second wavelength range enters the at least one fiber Bragg grating of the at least one optical fiber through the beam splitting and combining element, after the second light passes through the at least one fiber Bragg grating and is focused on the to-be-tested object by the focusing element, the second light is reflected by the to-be-tested object to form a second reflected light, the second reflected light sequentially passes through the focusing element, the at least one optical fiber, and the beam splitting and combining element, the second reflected light is split by the beam splitting and combining element and transmitted to the object detecting module,
 wherein the first wavelength range is different from the second wavelength range,
 wherein the first wavelength range has a first peak wavelength and a first full width at tenth maximum, and the second wavelength range has a second peak wavelength and a second full width at tenth maximum, the wavelength range of the first full width at tenth maximum of positive/negative one-half of the first peak wavelength and the wavelength range of the second full width at tenth maximum of positive/negative one-half of the second peak wavelength are not overlapped with each other.

9. The optical system of claim 1, further comprising a plurality of functional tubes, and the at least one optical fiber is a plurality of optical fibers, wherein the catheter has a plurality of regions therein, and each of the regions is configured with one of the functional tubes and one of the optical fibers.

10. The optical system of claim 1, wherein the at least one fiber Bragg grating is a plurality of fiber Bragg gratings, and the fiber Bragg gratings are disposed along an axial extension direction of the gratings,
 wherein each of the fiber Bragg gratings includes a first portion and a second portion, a refractive index of the first portion is different from a refractive index of the second portion, and the first portion and the second portion are disposed along the axial extension direction,
 wherein a period of each of the fiber Bragg gratings is defined as a distance between a first surface of the first portion and a second surface of the second portion corresponding to the first portion in the axial extension direction, the first surface faces the end of the optical fiber, and the second surface faces the other end of the optical fiber, the periods of the fiber Bragg gratings are different from each other.

* * * * *